(12) United States Patent
Furusawa et al.

(10) Patent No.: US 8,658,432 B2
(45) Date of Patent: Feb. 25, 2014

(54) SI/SI3N4 SYSTEM NANOSIZED PARTICLES, BIOSUBSTANCE LABELING AGENT EMPLOYING THE NANOSIZED PARTICLES, AND METHOD OF MANUFACTURING THE NANOSIZED PARTICLES

(75) Inventors: Naoko Furusawa, Tokyo (JP); Yasushi Nakano, Tokyo (JP); Kazuya Tsukada, Tokyo (JP)

(73) Assignee: Konica Minolta Medical & Graphic, Inc. (JP)

( * ) Notice: Subject to any disclaimer, the term of this patent is extended or adjusted under 35 U.S.C. 154(b) by 1031 days.

(21) Appl. No.: 12/162,032

(22) PCT Filed: Jan. 23, 2007

(86) PCT No.: PCT/JP2007/050971
§ 371 (c)(1),
(2), (4) Date: Jul. 24, 2008

(87) PCT Pub. No.: WO2007/086367
PCT Pub. Date: Aug. 2, 2007

(65) Prior Publication Data
US 2009/0061536 A1 Mar. 5, 2009

(30) Foreign Application Priority Data
Jan. 27, 2006 (JP) .................................. 2006-019804

(51) Int. Cl.
*G01N 33/543* (2006.01)
*G01N 33/552* (2006.01)
*G01N 21/00* (2006.01)
(52) U.S. Cl.
USPC ......... 436/523; 436/527; 422/82.05; 977/773
(58) Field of Classification Search
None
See application file for complete search history.

(56) References Cited

U.S. PATENT DOCUMENTS

| 5,508,540 | A * | 4/1996 | Ikeda et al. ................... 257/298 |
| 5,663,087 | A * | 9/1997 | Yokozawa .................... 438/762 |
| 2004/0112964 | A1* | 6/2004 | Empedocles et al. ......... 235/491 |
| 2004/0152011 | A1* | 8/2004 | Chen et al. ................. 430/270.1 |
| 2005/0129580 | A1* | 6/2005 | Swinehart et al. ............ 422/100 |
| 2006/0182966 | A1* | 8/2006 | Lee et al. ....................... 428/375 |
| 2007/0269380 | A1* | 11/2007 | Zhang et al. ................. 424/9.32 |
| 2010/0255462 | A1* | 10/2010 | Tsukada et al. .................. 435/6 |

FOREIGN PATENT DOCUMENTS

| JP | 59-206042 A | 11/1984 |
| JP | 11-24079 A | 1/1999 |
| JP | 2003-329686 A | 11/2003 |
| JP | 2005-56705 A | 3/2005 |
| JP | 2005-172429 A | 6/2005 |
| WO | WO 2005041747 A2 * | 5/2005 |

OTHER PUBLICATIONS

International Search Report for International Application No. PCT/JP2007/050971 mailed May 15, 2007.

* cited by examiner

*Primary Examiner* — Shafiqul Haq
*Assistant Examiner* — Gary E Hollinden
(74) *Attorney, Agent, or Firm* — Cantor Colburn LLP

(57) ABSTRACT

An objective is to provide $Si/Si_3N_4$ system nanosized particles each exhibiting reduced environmental load together with minimized bio toxicity, excellent chemical stability, enhanced relative light emission intensity, and less degradation of emission intensity during continuous exposure to light; a biosubstance labeling agent capable of keeping on labeling a biosubstance exhibiting luminance enhanced for a long duration with the $Si/Si_3N_4$ system nanosized semiconductor particle of the present invention; and also a method of manufacturing the $Si/Si_3N_4$ system nanosized semiconductor particle of the present invention.

6 Claims, No Drawings

US 8,658,432 B2

SI/SI3N4 SYSTEM NANOSIZED PARTICLES, BIOSUBSTANCE LABELING AGENT EMPLOYING THE NANOSIZED PARTICLES, AND METHOD OF MANUFACTURING THE NANOSIZED PARTICLES

CROSS REFERENCE TO RELATED APPLICATIONS

This is a U.S. national stage of application No. PCT/JP2007/050971, filed on 23 Jan. 2007. Priority under 35 U.S.C. §119(a) and 35 U.S.C. §365(b) is claimed from Japanese Application No. 2006-019804, filed 27 Jan. 2006, the disclosure of which is also incorporated herein by reference.

TECHNICAL FIELD

The present invention relates to $Si/Si_3N_4$ system nanosized particles, a biosubstance labeling agent employing the nanosized particles, and a method of manufacturing the nanosized particles.

BACKGROUND

Since nanosized semiconductor particles each have a particle diameter in the order of nanometers, it is known that a quantum size effect to increase band gap energy and so forth is produced, resulting in optical properties, exhibiting a light absorption property and light emission property, for example. Not only active studies of nanosized semiconductor particles have recently been made, but also studies of nanosized semiconductor particles such as CdSe/ZnS type nanosized semiconductor particles, $Si/SiO_2$ system nanosized semiconductor particles and the like have been in progress for various uses such as displays or LED.

On the one hand, as a means to label a biosubstance, studied has been a method with a biosubstance labeling agent in which a molecular label substance was bonded to a marker substance. However, the marker substance used in the above-described method, such as organic fluorescence dyes, exhibited disadvantages of large degradation and short life during exposure to UV light, and resulted also in low emission efficiency and insufficient sensitivity.

Accordingly, attention has recently been focused on a method with nanosized semiconductor particles used as the above-described marker substance. For instance, studied has been a biosubstance labeling agent, in which a polymer containing a polar functional group is physically and/or chemically attached onto the surface of nanosized semiconductor particles (refer to Patent Document 1, for example).

On the other hand, also studied has been a biosubstance labeling agent in which an organic molecule is bonded to the surface of $Si/SiO_2$ system nanosized semiconductor particles (refer to Patent Document 2, for example).

However, there appeared a problem against a biosubstance labeling agent employing these conventional nanosized semiconductor particles.

For example, nanosized semiconductor particles disclosed actually in Patent Document 1 with respect to the effect are (CdSe/ZnS system) nanosized semiconductor particles, but when they are used as a biosubstance labeling agent, those used as the biosubstance labeling agent have produced a problem since reduced environmental load together with minimized bio toxicity associated with a material used for the nanosized semiconductor particle, specifically CdSe, has been pointed out, though the particle surface is covered with organic molecules.

In the case of $Si/SiO_2$ system nanosized semiconductor particles disclosed in Patent Document 2, the core is made of Si, but Si tends to be oxidized, depending on the environment despite the fact that a core made of Si is covered by a shell made of $SiO_2$ (reaction between Si and oxygen in an aqueous dispersion) since nanosized semiconductor particles are commonly utilized in the presence of oxygen, whereby there is still room for improvement.

Patent Document 1: Japanese Patent O.P.I. Publication No. 2003-329686.

Patent Document 2: Japanese Patent O.P.I. Publication No. 2005-172429.

DISCLOSURE OF THE INVENTION

Problems to be Solved by the Invention

The present invention has been made on the basis of the above-described situation, and it is an object of the present invention to provide $Si/Si_3N_4$ system nanosized particles each exhibiting reduced environmental load together with minimized bio toxicity, excellent chemical stability, enhanced relative light emission intensity, and less degradation of emission intensity during continuous exposure to light; a biosubstance labeling agent capable of keeping on labeling a biosubstance exhibiting luminance enhanced for a long duration with the $Si/Si_3N_4$ system nanosized semiconductor particle of the present invention; and also a method of manufacturing the $Si/Si_3N_4$ system nanosized semiconductor particle of the present invention.

Means to Solve the Problems

The above-described object of the present invention was accomplished by the following structures.

(Structure 1) A $Si/Si_3N_4$ system nanosized particle comprising a core made of Si and a shell made of $Si_3N_4$, wherein the $Si/Si_3N_4$ system nanosized particle has a core diameter of 1-50 nm.

(Structure 2) The $Si/Si_3N_4$ system nanosized particle of Structure 1, wherein the shell has a thickness of 1-50 nm.

(Structure 3) The $Si/Si_3N_4$ system nanosized particle of Structure 1 or 2, wherein a surface of the shell is subjected to a hydrophilization treatment.

(Structure 4) A biosubstance labeling agent comprising bonding of the $Si/Si_3N_4$ system nanosized particle of Structure 3 to a molecular label substance via an organic molecule.

(Structure 5) The biosubstance labeling agent of Structure 4, wherein the molecular label substance comprises a nucleotide chain.

(Structure 6) The biosubstance labeling agent of Structure 4, wherein the molecular label substance comprises an antibody.

(Structure 7) The biosubstance labeling agent of Structure 4, wherein the organic molecule is biotin or avidin.

(Structure 8) A method of manufacturing the $Si/Si_3N_4$ system nanosized particle of Structure 1 or 2, comprising the step of conducting a vapor phase reaction between monosilane gas and ammonia.

Effect of the Invention $Si/Si_3N_4$ system nanosized semiconductor particles each exhibiting reduced environmental load together with minimized bio toxicity, excellent chemical stability, enhanced relative light emission intensity, and less deterioration of emission intensity during continuous exposure to light were able to be obtained in the present invention. Also obtained can be a biosubstance labeling agent capable of keeping on labeling a biosubstance exhibiting luminance enhanced for a long duration with the $Si/Si_3N_4$ system nanosized semiconductor particles of the present invention.

DESCRIPTION OF THE PREFERRED EMBODIMENTS

According to a $Si/Si_3N_4$ system nanosized semiconductor particle of any one of Structures 1-3 in the present invention, $Si/Si_3N_4$ system nanosized semiconductor particles each exhibiting reduced environmental load together with minimized bio toxicity, excellent chemical stability, enhanced relative light emission intensity, and less degradation of emission intensity during continuous exposure to light were able to be obtained. Also provided can be a biosubstance labeling agent capable of keeping on labeling a biosubstance exhibiting luminance enhanced for a long duration with the $Si/Si_3N_4$ system nanosized semiconductor particle.

Next, each of constituent elements in the present invention will be detailed in order.

The inventors have found out during their studies of the above-described subject that nanosized semiconductor particles each in which the core is made of Si, and the shell is made of $Si_3N_4$ exhibit reduced environmental load together with minimized bio toxicity, excellent chemical stability, and excellent optical properties such as relative light emission intensity and so forth, and have accomplished the present invention.

<<$Si/Si_3N_4$ System Nanosized Particle>>

$Si/Si_3N_4$ system nanosized particles of the present invention will be described.

As described in Structure 1, each of $Si/Si_3N_4$ system nanosized particles of the present invention possesses a core made of Si, and a shell made of $Si_3N_4$, and the $Si/Si_3N_4$ system nanosized particle has a core diameter of 1-50 nm.

<<Core>>

A core of a $Si/Si_3N_4$ system nanosized particle in the present invention is made of Si. A diameter of the core made of Si is in the range of 1-50 nm, but preferably in the range of 1-20 nm, and more preferably in the range of 2-12 nm.

The core form is formed from Si crystals, and they may be single crystals or polycrystals, but single crystals are more preferable than polycrystals since the half-value width of an emission spectrum becomes narrow.

Purity of Si of which the core is made is conventionally a Si content of at least 90%, preferably a Si content of at least 95%, and more preferably a Si content of at least 99%.

In cases where a core diameter of a $Si/Si_3N_4$ system nanosized particle in the present invention is at least the lower limit value of the above-described range, the particle diameter can be easily controlled, resulting in reduced variation of the particle diameter. Further, in cases where the core diameter is the upper limit value or less of the above-described range, excellent optical properties such as enhanced light emission efficiency and so forth can be obtained.

<<Shell>>

A shell of a $Si/Si_3N_4$ system nanosized particle in the present invention is made of $Si_3N_4$. It is preferable that there appear excellent properties such that $Si_3N_4$ has a larger bandgap than that of Si, and has a higher stability with respect to oxygen than that of $SiO_2$, whereby degradation performance during UV exposure in the aqueous dispersion is largely improved.

The foregoing shell preferably has a thickness of 1-50 nm, and more preferably has a thickness of 1-20 nm. In cases where the shell thickness is larger than the lower limit value of the above-described range, the shell thickness is sufficient, whereby chemical reaction between Si and another substance, degradation of light emission intensity during continuous exposure to light, and so forth can be effectively prevented.

Further, in cases where the shell thickness is smaller than the upper limit value of the above-described range, nanosized particles exhibit sufficient optical properties.

(Hydrophilization Treatment for Shell)

In the case of a shell formed from $Si_3N_4$ in the present invention, the surface may be subjected to a hydrophilization treatment, and $Si/Si_3N_4$ system nanosized particles having been subjected to such the hydrophilization treatment can be utilized as a biosubstance labeling agent by bonding via a molecular labeling substance and organic molecules.

Incidentally, the hydrophilization treatment for shells and the biosubstance labeling agent will be described in detail later on.

In addition, though the term "A/B system nanosized particles" is used in the present specification, this means nanosized particles each in which a core is made of A, and a shell is made of B. For example, $Si/Si_3N_4$ system nanosized particles mean nanosized particles each in which the core is made of Si, and the shell is made of $Si_3N_4$.

<<Method of Manufacturing $Si/Si_3N_4$ System Nanosized Particles>>

A method of manufacturing $Si/Si_3N_4$ system nanosized particles of the present invention will be described.

The method of manufacturing $Si/Si_3N_4$ system nanosized particles of the present invention may be a method of manufacturing via vapor phase reaction, for example.

In cases where $Si/Si_3N_4$ system nanosized particles are manufactured via vapor phase reaction, monosilane gas and ammonia are mixed with inert gas to yield a reaction at high temperature and low pressure. Then, annealing is conducted in inert gas atmosphere at high temperature and atmospheric pressure to accelerate crystallization, whereby an excessive amount of silicon forms a core in the inside of a particle, and a shell is formed by pushing silicon nitride out to obtain the $Si/Si_3N_4$ system nanosized particle.

Examples of the above-described usable inert gas include nitrogen, argon, neon and so forth.

The above-described high temperature and low pressure of a temperature of 500-850° C. and a pressure of 1-80 kPa is preferable, and reaction at a temperature of 700° C. and a pressure of 50 kPa is, for example, preferable.

As to the above-described high temperature and atmospheric pressure, a pressure of 91-112 kPa is preferable, and temperature is preferably adjusted to a temperature of 900-1400° C.

In the case of a large core diameter obtained via sufficient core-forming reaction, at least one of high annealing temperature and long annealing time is desired. Further, in cases where the entire particle diameter is large, the approximately identical size of core is formed in comparison to the cases where the entire particle diameter is small, by using at least one of high annealing temperature and long annealing time.

Further, the shell thickness with respect to the particle diameter of the resulting $Si/Si_3N_4$ system nanosized particle is possible to be adjusted by changing the content ratio of the above-described monosilane gas to ammonia.

For example, in the case of "monosilane gas:ammonia=1: 0.4" (by volume), the shell thickness with respect to the particle diameter of a $Si/Si_3N_4$ system nanosized particle results nearly in "core diameter:shell thickness=7:1", in the case of "monosilane gas:ammonia=1.1:1.08" (by volume), the shell thickness with respect to the particle diameter of a Si/Si$_3$N$_4$ system nanosized particle results nearly in "core diameter:shell thickness=4:2.5", and in the case of "monosilane gas:ammonia=1:1.3" (by volume), the shell thickness with respect to the particle diameter of a Si/Si$_3$N$_4$ system nanosized particle results nearly in "core diameter:shell thickness=2:3.5".

The particle diameter of particles is controlled by reaction temperature and a supply rate of monosilane.ammonia gas. The higher the temperature, the larger the particle diameter is, and the larger the gas supply amount per unit time, the smaller the particle diameter is.

<<Structure and Properties of Si/Si$_3$N$_4$ System Nanosized Particles>>

The structure and properties of Si/Si$_3$N$_4$ system nanosized particles in the present invention will be described.

The entire Si/Si$_3$N$_4$ system nanosized particle preferably has a particle diameter of 2-60 nm, and more preferably has a particle diameter of 3-20 nm. A particle diameter falling within the foregoing range, which is nearly equivalent to the size of DNA or an antibody being the object of labeling, is preferred.

The Si/Si$_3$N$_4$ system nanosized particles each exhibit reduced environmental load together with minimized biotoxicity, chemical reaction less likely produced such as deteriorated reaction, enhanced relative light emission intensity, and less degradation of emission intensity during continuous exposure to light.

<<Hydrophilization Treatment for Si/Si$_3$N$_4$ System Nanosized Particles>>

The hydrophilization treatment for Si/Si$_3$N$_4$ system nanosized particles of the present invention will be described.

The shell surface of the above-described Si/Si$_3$N$_4$ system nanosized particle of the present invention exhibits hydrophobicity, and when used as a biosubstance labeling agent, the nanosized particles are poorly dispersed in water, producing a problem such that the particles are coagulated. Accordingly, it is preferable that the shell surface of the Si/Si$_3$N$_4$ system nanosized particle is subjected to a hydrophilization treatment.

As a hydrophilization treatment method, there is a method in which a surface modifying agent is adsorbed onto the particle surface. Specifically, Si/Si$_3$N$_4$ system nanosized particles are dispersed in pure water in which a mercaptoundecanoic acid is dissolved, and the shell surface is treated to modify the shell surface of the Si/Si$_3$N$_4$ system nanosized particle with a carboxyl group.

<<Biosubstance Labeling Agent>>

The biosubstance labeling agent of the present invention will be described. The biosubstance labeling agent of the present invention is obtained by bonding the Si/Si$_3$N$_4$ system nanosized particle having been subjected to the foregoing hydrophilization treatment to a molecular label substance via an organic molecule.

(Molecular Label Substance)

The biosubstance labeling agent of the present invention is possible to label a biosubstance when a molecular label substance is specifically bonded to and/or reacted with a target biosubstance.

Examples of the molecular label substance include a nucleotide chain, antibody, antigen and cyclodextrin.

(Organic Molecule)

The biosubstance labeling agent of the present invention is obtained by bonding the Si/Si$_3$N$_4$ system nanosized particle having been subjected to a hydrophilization treatment to a molecular label substance via an organic molecule. The organic molecule is not specifically limited, provided that it is capable of allowing the Si/Si$_3$N$_4$ system nanosized particle to be bonded to the molecular label substance, but an albumin, myoglobin, casein and the like, for example, are preferable among proteins. Further, use in combination of avidin as a kind of protein with biotin is also preferable. Modes of the above-described bonding are not specifically limited, and include a covalent bond, ionic bond, hydrogen bond, coordination bond, physical adsorption, chemical adsorption and so forth. Strong bonding such as a covalent bond is preferred in terms of bonding stability.

Specifically, when the Si/Si$_3$N$_4$ system nanosized particle is hydrophilized with mercaptoundecanoic acid, avidin and biotin can be utilized as the organic molecule. Thus, a carboxyl group in the Si/Si$_3$N$_4$ system nanosized particle having been subjected to the hydrophilization treatment is covalently bonded to avidin suitably; the avidin is further bonded selectively to biotin, while the biotin is bonded to a biosubstance labeling agent to form the biosubstance labeling agent.

EXAMPLE

Next, the present invention will be explained referring to examples, but the present invention is not limited thereto.

Example 1

<<Preparation of Si/Si$_3$N$_4$ System Nanosized Particle 1>>

A mixed gas including 0.70 l/min of monosilane gas, 19.00 l/min of nitrogen gas, and 0.30 l/min of ammonia was introduced into a reaction tube made of quartz glass, which was maintained at a temperature of 700° C. and a pressure of 50 kpa, to yield reaction for 0.5 hours. In this case, powder was formed at the lower portion of the reaction tube.

The reaction tube was substituted by nitrogen gas to set to atmospheric pressure. The powder was subjected to an annealing treatment at 1100° C. for 2 hours while rotating the reaction tube.

After cooling the reaction tube down to room temperature, 100 ml of pure water and 0.5 mg of mercaptoundecanoic acid with respect to 1 mg of powder were added while stirring at 40° C. for 10 minutes to obtain Si/Si$_3$N$_4$ system nanosized particle 1 which was surface-hydrophilized with a carboxy group.

The resulting Si/Si$_3$N$_4$ system nanosized particles were observed employing a high-resolution TEM, whereby crystallization was confirmed since lattice images were confirmed. The average particle diameter of the entire Si/Si$_3$N$_4$ system nanosized particle (excluding the carboxyl group), the core particle diameter and the shell thickness were also measured. The results are shown in Table 1.

The XPS measurement of Si 2 p spectrum for the resulting Si/Si$_3$N$_4$ system nanosized particles was conducted, and as to the Si/Si$_3$N$_4$ system nanosized particles, a peak of Si—Si bonding and a peak of Si—N bonding were confirmed.

<<Preparation of Si/Si$_3$N$_4$ System Nanosized Particle 2>>

Si/Si$_3$N$_4$ system nanosized particle 2, which was surface-hydrophilized, was obtained similarly to Example 1, except that a mixed gas included 0.48 l/min of monosilane gas, 19.00 l/min of nitrogen gas, and 0.52 l/min of ammonia, and an annealing treatment was conducted at 1100° C. for one hour. The results are shown in Table 1.

<<Preparation of Si/Si$_3$N$_4$ System Nanosized Particle 3>>

Si/Si$_3$N$_4$ system nanosized particle 3, which was surface-hydrophilized, was obtained similarly to Example 1, except that a mixed gas included 0.43 l/min of monosilane gas, 19.00 l/min of nitrogen gas, and 0.57 l/min of ammonia, and an annealing treatment was conducted at 1100° C. for 0.5 hours. The results are shown in Table 1.

<<Preparation of Si/Si$_3$N$_4$ System Nanosized Particle 4>>

Si/Si$_3$N$_4$ system nanosized particle 4, which was surface-hydrophilized, was obtained similarly to Example 1, except that a mixed gas included 1.44 l/min of monosilane gas, 18.00 l/min of nitrogen gas, and 0.56 l/min of ammonia, reaction temperature was set to 650° C., and an annealing treatment was conducted at 1000° C. for one hour. The results are shown in Table 1.

<<Preparation of Si/Si$_3$N$_4$ System Nanosized Particle 5>>

Si/Si$_3$N$_4$ system nanosized particle 5, which was surface-hydrophilized, was obtained similarly to Example 1, except that a mixed gas included 0.09 l/min of monosilane gas, 19.80 l/min of nitrogen gas, and 0.11 l/min of ammonia, reaction temperature was set to 850° C., and an annealing treatment was conducted at 1250° C. for one hour. The results are shown in Table 1.

<<Preparation of Comparative Nanosized Particle 1>>

A mixed gas including 1.00 l/min of monosilane gas and 19.00 l/min of nitrogen gas was introduced into a reaction tube made of quartz glass, which was maintained at a temperature of 700° C. and a pressure of 50 kPa, to yield reaction for 0.5 hours. In this case, powder was formed at the lower portion of the reaction tube.

The reaction tube was substituted by nitrogen gas to set to atmospheric pressure. The powder was subjected to an annealing treatment at 1100° C. for one hour while rotating the reaction tube.

Next, after introducing 20 l/min of air at 800° C. for 10 minutes during falling of temperature, nitrogen-substitution was conducted again, and the reaction tube was cooled.

After cooling the reaction tube down to room temperature, 100 ml of pure water and 0.5 mg of mercaptoundecanoic acid with respect to 1 mg of powder were added while stirring at 40° C. for 10 minutes to obtain Si/SiO$_2$ system nanosized particles which were surface-hydrophilized with a carboxy group.

The resulting Si/SiO$_2$ system nanosized particles were observed employing a high-resolution TEM, whereby crystallization was confirmed since lattice images were confirmed. The average particle diameter of the entire Si/SiO$_2$ system nanosized particle (excluding the carboxyl group), the core particle diameter and the shell thickness were also measured. The results are shown in Table 1.

The XPS measurement of Si 2p spectrum for the resulting Si/Si$_3$N$_4$ system nanosized particles was conducted, and as to the Si/SiO$_2$ system nanosized particles, a peak of Si—Si bonding and a peak of Si—O bonding were confirmed.

Measuring apparatus: ESCAlab200R, manufactured by VG Scientific, Ltd

Measuring condition: Measurement conducted employing a specimen stage made of graphite

TABLE 1

| | Inflow gas amount | | | Temperature (° C.) | Annealing treatment | | Particle diameter (nm) | Core diameter (nm) | Shell thickness (nm) |
|---|---|---|---|---|---|---|---|---|---|
| | SiH$_4$ l/min | NH$_3$ l/min | N$_2$ l/min | | Temperature (° C.) | Time (h) | | | |
| Si/Si$_3$N$_4$ system nanosized particle 1 | 0.70 | 0.30 | 19.00 | 700 | 1100 | 2 | 9 | 7 | 1 |
| Si/Si$_3$N$_4$ system nanosized particle 2 | 0.48 | 0.52 | 19.00 | 700 | 1100 | 1 | 9 | 4 | 2.5 |
| Si/Si$_3$N$_4$ system nanosized particle 3 | 0.43 | 0.57 | 19.00 | 700 | 1100 | 0.5 | 9 | 2 | 3.5 |
| Si/Si$_3$N$_4$ system nanosized particle 4 | 1.44 | 0.56 | 18.00 | 650 | 1000 | 1 | 5 | 4 | 0.5 |
| Si/Si$_3$N$_4$ system nanosized particle 5 | 0.09 | 0.11 | 19.80 | 850 | 1250 | 1 | 48 | 4 | 22 |
| Si/SiO$_2$ system nanosized particle | 1.00 | 0.00 | 19.00 | 700 | 1100 | 1 | 9 | 4 | 2.5 |

Example 2

Light emission properties of the resulting surface-hydrophilized Si/Si$_3$N$_4$ system and Si/SiO$_2$ system nanosized particles were measured by a method as described below.

Employing a Hitachi spectrophotofluorometer F-7000, 6 kinds of the foregoing nanosized particles each were measured with respect to its emission spectrum at an excitation wavelength of 365 nm to make a comparison of the peak wavelength intensity.

Further, as to 6 kinds of the nanosized particles, alteration of the emission spectrum with time was measured, and the relative light emission intensity after one hour was obtained when the initial light emission intensity of each of the 6 ns was set to 100.

The obtained results are shown in Table 2.

TABLE 2

| | Light emission wave length | Light emission intensity *1 | Light emission intensity after one hour *2 |
|---|---|---|---|
| Si/Si$_3$N$_4$ system nanosized | 620 nm | 102 | 96 |

TABLE 2-continued

| | Light emission wave length | Light emission intensity *1 | Light emission intensity after one hour *2 |
|---|---|---|---|
| particle 1 Si/Si$_3$N$_4$ system nanosized particle 2 | 510 nm | 100 | 95 |
| Si/Si$_3$N$_4$ system nanosized particle 3 | 410 nm | 101 | 94 |
| Si/Si$_3$N$_4$ system nanosized particle 4 | 510 nm | 95 | 80 |
| Si/Si$_3$N$_4$ system nanosized particle 5 | 510 nm | 88 | 95 |
| Si/SiO$_2$ system nanosized particle | 510 nm | 93 | 75 |

*1: relative light emission intensity when the initial light emission intensity of Si/Si$_3$N$_4$ system nanosized particle 2 was set to 100
*2: Relative light emission intensity after one hour when the initial light emission intensity of each of the 6 kinds was set to 100

Example 3

<<Preparation of Biosubstance Labeling Agent>>

Into an aqueous solution of the surface-hydrophilized Si/Si$_3$N$_4$ system nanosized particle 2 of the present invention, added was 25 mg of avidin while stirring at 40° C. for 10 minutes to prepare avidin-conjugated Si/Si$_3$N$_4$ system nanosized particles.

The resulting avidin-conjugated nanosized particles were mixed with a biotin-attached oligonucleotides having a known base sequence to prepare oligonucleotide labeled with nanosized particles.

When the labelled oligonucleotide described above was dropwise added onto a DNA tip in which nucleotide having various base sequences was fixed, and washed, only a spot of oligonucleotide having complementary base sequence to the labeled oligonucleotide produced luminescence via exposure to ultraviolet rays.

This was able to confirm labeling of oligonucleotide with nanosized particles.

The invention claimed is:

1. A Si/Si$_3$N$_4$ system nanosized particle comprising a core made of Si and a shell made of Si$_3$N$_4$ about an entire surface of the core,
   wherein the Si/Si$_3$N$_4$ system nanosized particle has a core diameter of 1-50 nm, and wherein an entire surface of the shell is subjected to a hydrophillization treatment.

2. The Si/Si$_3$N$_4$ system nanosized particle of claim 1, wherein the shell has a thickness of 1-50 nm.

3. A biosubstance labeling agent comprising bonding of the Si/Si$_3$N$_4$ system nanosized particle of claim 1 to a molecular label substance via an organic molecule.

4. The biosubstance labeling agent of claim 3, wherein the molecular label substance comprises an antibody.

5. The biosubstance labeling agent of claim 3, wherein the organic molecule is biotin or avidin.

6. A method of manufacturing the Si/Si$_3$N$_4$ system nanosized particle of claim 1, comprising the step of:
   conducting a vapor phase reaction between monosilane gas and ammonia.

* * * * *